US006410717B1

(12) United States Patent
Furusawa et al.

(10) Patent No.: US 6,410,717 B1
(45) Date of Patent: Jun. 25, 2002

(54) GENE ENCODING A HOST FACTOR PROTEIN INDISPENSABLE FOR MULTIPLICATION OF A PLANT VIRUS

(75) Inventors: Iwao Furusawa, Kyoto; Masayuki Ishikawa, Sapporo, both of (JP)

(73) Assignee: Kyoto University (JP)

( * ) Notice: Subject to any disclaimer, the term of this patent is extended or adjusted under 35 U.S.C. 154(b) by 0 days.

(21) Appl. No.: 09/420,786

(22) Filed: Oct. 19, 1999

(30) Foreign Application Priority Data

| | | |
|---|---|---|
| Oct. 23, 1998 | (JP) | 10-301810 |
| Aug. 19, 1999 | (JP) | 11-232678 |

(51) Int. Cl.[7] .......................... C07H 21/04; C12N 5/10

(52) U.S. Cl. ...................... 536/23.6; 536/23.1; 435/419

(58) Field of Search ................................ 800/278, 279, 800/295, 298, 301; 536/23.1, 23.6; 435/419, 69.1, 468

(56) References Cited

PUBLICATIONS

M. Ishikawa et al, "Effects of the tom1 Mutation of *Arabidopsis thaliana* on the Multiplication of Tobacco Mosaic Virus RNA in Protoplasts", *Journal of Virology* (Sep. 1993) vol. 67, No. 9, pp. 5328–5338.

*Primary Examiner*—Remy Yucel
*Assistant Examiner*—Konstantina Katcheves
(74) *Attorney, Agent, or Firm*—Burns, Doane, Swecker & Mathis, L.L.P.

(57) ABSTRACT

A gene effective to render virus resistance to a plant without risks of biological hazard is provided. This invention provides TOM1 gene (SEQ ID NO:2) which encodes TOM1 protein (SEQ ID NO:1). Furthermore, this invention provides TOM3 gene (SEQ ID NO:4) which encodes TOM3 protein (SEQ ID NO:3). The TOM1 gene and the TOM3 gene are derived from *Arabidopsis thaliana*. These encoded proteins are indispensable for multiplication of a tobacco mosaic virus. By alteration in these genes a transgenic plant can be produced which will have resistance against the tobacco mosaic virus.

4 Claims, 6 Drawing Sheets

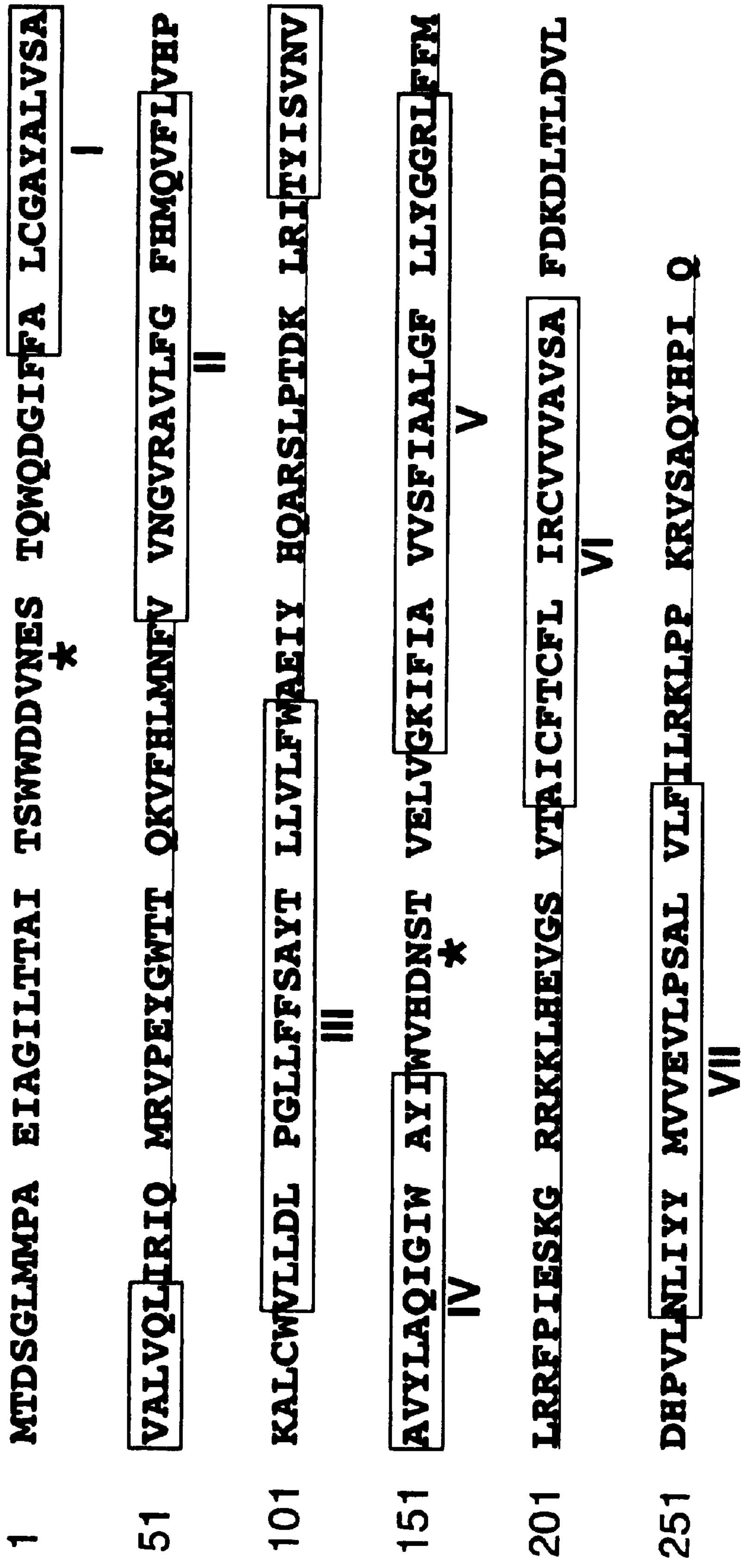

FIG. 3

```
1    MTDSGLMMPA EIAGILTTAI TSWWDDVNES TQWQDGIFFA LCGAYALVSA
                                      *                  ‾‾‾‾‾‾‾‾‾‾
                                                              I
51   VALVQLRIQ MRVPEYGWTT QKVFHLMNFV VNGVRAVLFG FHMQVFLVHP
     ‾‾‾‾‾‾‾‾‾                        ‾‾‾‾‾‾‾‾‾‾‾‾‾‾‾‾‾‾‾‾‾
                                                 II
101  KALCWVLLDL PGLLFFFSAYT LLVLFWAEIY HQARSLPTDK LRITYISVNV
                            ‾‾‾‾‾‾‾‾‾‾                ‾‾‾‾‾‾‾‾‾‾
                                III
151  AVYLAQIGIW AYIWHDNST  VELVGKIFIA VVSFIAALGF LLYGGRLFFM
     ‾‾‾‾‾‾‾‾‾‾‾‾‾‾‾‾‾‾‾                ‾‾‾‾‾‾‾‾‾‾‾‾‾‾‾‾‾‾‾‾‾
            IV      *                          V
201  LRRFPIESKG RRKKLHEVGS VTAICFTCFL IRCVVVAVSA FDKDLTLDVL
                                       ‾‾‾‾‾‾‾‾‾‾
                                          VI
251  DHPVLNLIYY MVVEVLPSAL VLFLRKLPP KRVSAQYHPI Q
                           ‾‾‾‾‾‾‾‾‾‾‾‾‾‾‾‾‾‾‾
                                   VII
```

FIG. 6

```
                10        20                    30        40
TOM1    MTDSGLMMPAEIAGILTTAITS------------WWDDVNESTQWQDGIFFALCGAYALV
        :  .:. .    . ..... .:            ::.:::::  ::: :: .:   :..:
TOM3    MRIGGVEVTKFASEMMSSSSSSAVEMLNLKEASNWWSDVNESPIWQDRIFHVLAVLYGIV
                10        20        30        40        50        60

        50        60        70        80        90       100
TOM1    SAVALVQLIRIQMRVPEYGWTTQKVFHLMNFVVNGVRAVLFGFHMQVFLVHPKALCWVLL
        : ::..::.:::.::::::::::::::..::::::::::.: :. .: ...:. :  .::
TOM3    SLVAVIQLVRIQLRVPEYGWTTQKVFHFLNFVVNGVRAVVFVFRRNVQFMQPEILQHILL
                70        80        90       100       110       120

       110       120       130       140       150       160
TOM1    DLPGLLFFSAYTLLVLFWAEIYHQARSLPTDKLRITYISVNVAVYLAQIGIWAYIWVHDN
        :.:.: ::..:.::::::::::.:::.. :: :: .....:..::..::..:  .: .
TOM3    DIPSLAFFTTYALLVLFWAEIYYQARAVSTDGLRPSFFTINAVVYVVQIALWLVLWWKPV
               130       140       150       160       170       180

       170       180       190       200       210       220
TOM1    STVELVGKIFIAVVSFIAALGFLLYGGRLFFMLRRFPIESKGRRKKLHEVGSVTAICFTC
         .. ...:.:.: ::..:::::::::::::.::.:::.:::::::::.::: ::.:::::
TOM3    RVMVILSKMFFAGVSLFAALGFLLYGGRLFLMLQRFPVESKGRRKKLQEVGYVTTICFTC
               190       200       210       220       230       240

       230       240       250       260       270       280
TOM1    FLIRCVVVAVSAFDKDLTLDVLDHPVLNLIYYMVVEVLPSALVLFILRKLPPKRVSAQYH
        :::::...  .:::.  .:::::::.::.:::..::.:::.:::::::::::::  .:::
TOM3    FLIRCIMMCFAAFDEGANLDVLDHPILNFIYYLLVEILPSSLVLFILRKLPPKRGITQYH
               250       260       270       280       290       300

       290
TOM1    PIQ
         :.
TOM3    QIR
```

GENE ENCODING A HOST FACTOR PROTEIN INDISPENSABLE FOR MULTIPLICATION OF A PLANT VIRUS

BACKGROUND OF THE INVENTION

1. Field of the Invention

This invention relates to TOM1 gene and TOM3 gene, which are host-encoded protein factors derived from *Arabidopsis thaliana* indispensable for the multiplication of a plant virus and relates to a transgenic plant wherein its virus resistance is enhanced.

2. Description of Related Art

Virus replication is suggested to take place through specific interaction among viral replication proteins, viral RNAs and host-encoded proteins. However, any host-encoded plant genes indispensable for the multiplication of viruses have not been identified.

Heretofore, a technique utilizing hypersensitive reaction have been adopted to render virus resistance to a plant. Concerning the technique, following problems should be solved prior to practical use.

(1) The virus resistance can not be rendered to a plant of other species.

(2) The virus resistance is only available for limited range of viruses.

(3) The frequent emergence of a mutated virus strain, which can conquer virus resistance of the host plant is hazardous biologically.

On the other hand, expression of a part of virus genome in a plant body to render virus resistance have came to a stage of practical use, following problems should be solved.

(1) The virus resistance is only available for limited range of viruses.

(2) The possible emergence of a novel virus strain by gene recombination is hazardous biologically.

SUMMARY OF THE INVENTION

The inventors have cloned *Arabidopsis thaliana* TOM1 and TOM3 genes, which encode proteins indispensable for the multiplication of a plant virus. The virus resistance might be rendered to a plant by expression regulation or alteration of TOM1 or TOM3 gene.

In anti-viral strategies utilized so far, many methods have not been used universally, because engineered virus resistance was specific to the virus species. The TOM1 gene of *Arabidopsis thaliana* was selected as a target gene, because the gene is a host plant-encoded gene indispensable for multiplication of a virus in a plant body. Therefore, it is assumed that, a gene with high homology would exist in other plant species and other alpha-like viruses of plants or animals would multiplicate using certain product of host-encoded gene similar to TOM1. From the assumption, production of an organism with virus resistance by manipulation of TOM1 gene or its homolog may be effective to resist against various kinds of alpha-like viruses. Moreover, emergence of a mutated virus strain which can conquer virus resistance of the host plant is not likely to occur, for this method inhibits essential interaction between the host plant and the virus.

In this invention, a mutant strain of *Arabidopsis thaliana*, with decreased accumulation of TMV-Cg CP by virus infection, was produced. The TOM1 gene, indispensable for the efficient multiplication of TMV, was obtained from the wild-type strain by positional cloning. Moreover, a nucleotide sequence of TOM1 gene and an amino acid sequence of TOM1 protein were determined. A double mutant strain of *Arabidopsis thaliana* was obtained by further mutagenesis of the tom1 mutant. In the double mutant strain, the activity to multiplicate tabacco mosaic virus remained in the tom1 mutant strain is completely abolished. TOM3 gene, which is indispensable for the multiplication of TMV in tom1 mutant, was obtained, and a nucleotide sequence of TOM3 gene and an amino acid sequence of TOM3 protein were determined. The anti-viral strategy of this invention is free from hazard of emergence of a novel virus strain by gene recombination, for gene manipulation of this method is limited to host plant-encoded gene. Therefore, the anti-viral strategy of this invention is expected to be effective and free from biological hazard, and this strategy would be of great application on agricultural or medical field.

The TOM1 gene of this invention is identified by a nucleotide sequence referred to sequence number 2 in a sequence list. The TOM1 protein, a polypeptide encoded by the TOM1 gene, is identified by an amino acid sequence referred to sequence number 1 in a sequence list. Moreover, the TOM3 gene of this invention is identified by a nucleotide sequence referred to sequence number 4 in a sequence list. The TOM3 protein, a polypeptide encoded by the TOM3 gene, is identified by an amino acid sequence referred to sequence number 3 in a sequence list. As described above, the TOM1 gene and the TOM3 gene are originated from *Arabidopsis thaliana* and the TOM1 protein and the TOM3 protein are host-encoded plant factors indispensable for multiplication of tabacco mosaic virus. Thus, virus resistance can be rendered to a plant, by expression regulation or alteration of the genes of this invention and the genes of this invention can be used for such purpose. For example, anti-sense RNA of TOM1, TOM3 or both genes would be available, and expression regulation of TOM1, TOM3 or both genes by using the technique of co-suppression would be also available. Moreover, virus resistance can be rendered to a plant, by incorporation of mutated tom1, tom3 or both genes encoding proteins capable of interacting with a virus but not capable of supporting multiplication of a virus. Such mutation can cause dominant-negative effect on the function of TOM1, TOM3 or both genes.

In general, one amino acid is encoded by plural base sequences of DNA. Therefore, plural genes, other than native gene of this invention, might encode amino acid sequence identical to TOM1 or TOM3 protein. The genes of this invention are not to be limited to only native genes and intended to include many other base sequences encoding TOM1 or TOM3 protein.

The TOM1 protein of this invention includes a polypeptide having an amino acid sequence at least 50% of sequence homology with the amino acid sequence referred to sequence number 1 in a sequence list, as far as having the activity to support the multiplication of alpha-like virus. In preferred form, the precursor polypeptide of this invention have more than 70% of sequence homology with the amino acid sequence referred to sequence number 1 in a sequence list. In more preferred form, the precursor polypeptide of this invention have more than 90% of sequence homology with the amino acid sequence referred to sequence number 1 in a sequence list.

In the same manner, The TOM3 protein of this invention includes a polypeptide having an amino acid sequence at least 50% of sequence homology with the amino acid sequence referred to sequence number 3 in a sequence list, as far as having the activity to multiplicate alpha-like virus. In preferred form, the precursor polypeptide of this invention have more than 70% of sequence homology with the amino acid sequence referred to sequence number 3 in a sequence list. In more preferred form, the precursor polypeptide of this invention have more than 90% of sequence homology with the amino acid sequence referred to sequence number 3 in a sequence list.

Using the recombinant DNA technique, a DNA can be mutated artificially at a certain position without alteration or with improvement of basic characteristic of a protein encoded by the nucleotide sequence of the DNA. Concerning genes having native nucleotide sequences provided by this invention, and other genes having base sequences encoding TOM1 or TOM3 protein, these sequences can be altered artificially by insertion, deletion or substitution of the sequences, so far as retaining characteristic equivalent or improved compared to the native proteins. It is to be understood that mutated genes described above are in the range of this invention.

Therefore, the gene of this invention includes a gene that encodes the TOM1 protein described above consisting of a base sequence that hybridizes with the nucleotide sequence referred to sequence number 2 in a sequence list under a contingent condition.

In the same manner, the gene of this invention includes a gene that encodes the TOM3 protein described above consisting of a nucleotide sequence that hybridizes with the base sequence referred to sequence number 4 in a sequence list under a contingent condition.

Moreover, a transgenic plant wherein the gene of this invention is incorporated is also in the range of this invention. For the examples of plants preferable for incorporation of the genes of this invention, monocotyledonous plants such as rice, barley, wheat or corn and dicotyledonous plants such as eggplant, tomato and potato can be mentioned. For the examples of methods preferred to be adopted for incorporation of genes of this invention, agrobacterium method, protoplast-PEG method, protoplast-electroporation method, particle gun method and micro-injection method can be mentioned. This invention will be described in more details by following embodiment, above description and below embodiment are not intended to limit the range of this invention and intended to include ordinal alteration in the art.

BRIEF DESCRIPTION OF THE DRAWINGS

FIG. 3 is a figure showing deduced amino acid sequence of TOM1 protein.

FIG. 6 is a figure showing deduced amino acid sequences of TOM1 protein and TOM3 protein, in comparison of both sequences.

DETAILED DESCRIPTION OF THE DRAWINGS

Map-based Cloning of TOM1

In a previous study, the tom1 mutation was mapped to the long arm of chromosome 4 near the DNA marker JGB9 [K. Ohshima et al., Virology 243, 472 (1998)]. In order to map the tom1 mutation more precisely, the inventors screened approximately 3,000 F2 plants resulting from a cross between ecotype Col-0 plants and tom1–3 (derived from ecotype WS) mutant plants for those having chromosomal recombination between DNA markers g3883 and T18ISX (FIG. 1A).

Figure 1:
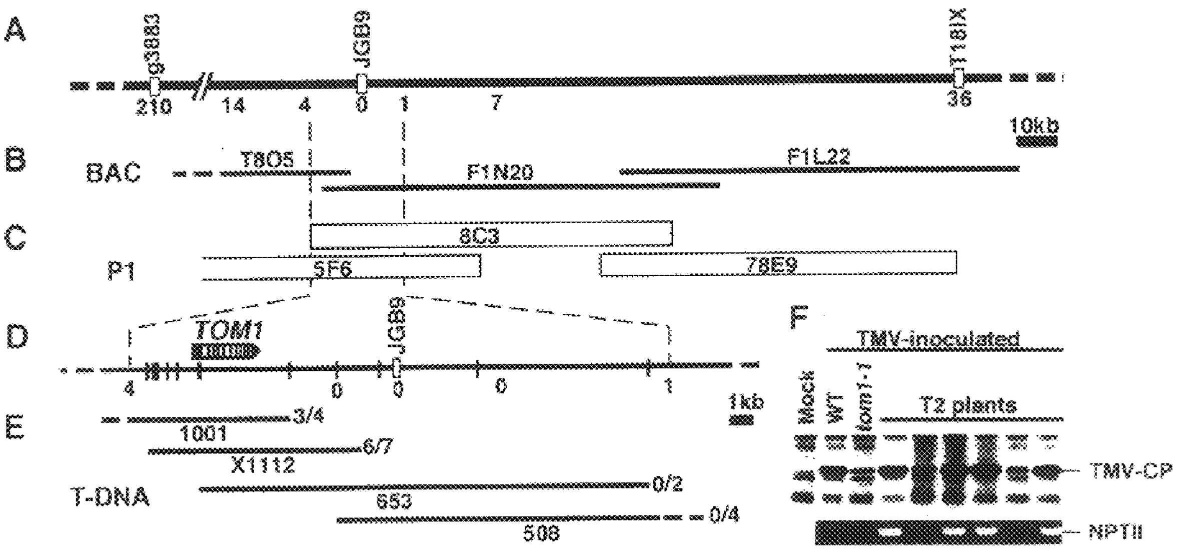
FIG. 1 is a schematic figure showing mapping and positional cloning of TOM1 gene.

As the result, 246 F2 recombinants were obtained, and the recombination between the TOM1 locus and the DNA markers shown in FIG. 1 was examined.

Genetic mapping and positional cloning of TOM1 is shown in FIG. 1.

(A) : Genetic map around the TOM1 locus on chromosome 4. Boxes represent CAPS markers. Each number represents the relative position of a marker and recombination events between that marker and the TOM1 locus.

(B) and (C) : Contigs of ESSA II BAC clones and Mitsui P1 clones encompassing the TOM1 locus, respectively.

(D) Physical map around the TOM1 locus. Vertical bars represent the EcoRI sites. Box and numbers are the same as in (A). The position, orientation and intron/exon organization of TOM1 is shown by the arrow, in which white boxes indicate introns.

(E) : T-DNA contigs. T-DNA clones derived from the P1 clones 8C3 or 5F6 were organized into an overlapping set that spanned the TOM1 locus. These T-DNA clones were used to genetically transform tom1–1 mutant plants, which were subsequently tested for complementation of the TMV multiplication phenotype. The ratio of numbers of transformed lines which showed wild-type level TMV multiplication vs total lines tested for TMV multiplication is indicated at the right of each T-DNA clone.

(F): Co-segregation of tom1 complementation with T-DNA. T2 progenies derived from a tom1 mutant transformed with T-DNA clone 1001 was inoculated with TMV-Cg. Two weeks after inoculation, total protein was prepared, separated by SDS-PAGE and stained with Coomassie brilliant blue (upper panel: M. Ishikawa, F. Obata, Obata, T. Kumagai, T. Ohno, Mol. Gen. Genet. 230, 33 (1991)). For each T2 plant, the NPTII gene sequence was amplified from purified DNA by PCR using specific primer sets (5'-CTATGACTGGGCACAACAGACAATC-3') (SEQ ID NO:5) and (5'-GCGATAGAAGGCGATGCGCT-3') (SEQ ID NO:6), and analyzed by agarose gel electrophoresis followed by ethidium bromide staining (lower panel). The positions of TMV-Cg CP and the PCI-amplified NPTII DNA fragment are indicated.

The CAPS marker T 28ISX (FIG. 1A) which gave an XbaI fragment length polymorphism between ecotypes Col-0 and WS, was created based on the finding that the end probe of the P1 clone 78E9 (FIG. 1C) showed an XbaI fragment length polymorphism between Col-0 and WS, and on the sequence information from the ESSA II BAC contig (FIG. 1B). Primers for T18ISX were, T18ISXF (5'-CTGAGAATGTTTATCCCAGCTG-3')(SEQ. ID No.:7) and T18ISXR (5'-GTAATGCTTGAATCTCTTGATATC-3') (SEQ. ID No: 8). The PCR markers, g3883 and JGB9 are described in the *Axabidopsis thaliana* Database (AtDB). The *A. thaliana* tom1-3 mutant was isolated by screening the Feldmann T-DNA-insertion library [K. A. Feldmann and M. D. Marks, Mol. Gen. Genet. 208, 1 (1987)] for mutants with low-level accumulation of TMV-Cg coat protein (CP). The tom1-3 plants showed similar accumulation patterns of TMV-Cg CP to those in *A. thaliana* tom1 and tom1-2 plants. Genetic analysis suggested the causal mutation was within the TOM1 locus. The tom1-3 mutation was not linked with the T-DNA insertion. Fine mapping of the TOM1 locus was performed using the tom1-3 mutant as follows: DNA was prepared from one of the leaves of each F2 plant derived from a cross between tom1-3 (derived from ecotype WS) and the *A. thaliana* ecotype Col-0 using the NaOH extraction method [H. Wang, M. Qi, A. J. Cutler, Nucleic Acids Res. 21, 4153 (1993)]. The genotype for markers g3 883 and T 1234 8ISX was subsequently examined for each F2 plant, and from 3103 original F2 plants, 246 plants which had a chromosomal recombination between these two markers were selected. DNA was then obtained from five leaves of each selected F2 plant, using the CTAB extraction method [S. O. Rogers and J. Bendich, Plant Mol. Biol. 5, 69 (1985)], and purified by chloroform extraction, isopropanol precipitation and MgCl2 precipitation [T. Yamamoto and M. Horikoshi, Nucleic Acids Res. 23, 3351 (1995)]. Using this DNA, genotypes for the CAPS marker JGB9 and RFLP markers indicated in FIG. 1 were determined. The RFLP markers were prepared from the P1 genomic clones by restriction digestion. Information on the RFLP markers is available upon request. Preparation of probes and Southern hybridization were carried out using a Gene Images labeling and detection system (Amersham Pharmacia Biotech, Uppsala, Sweden). The TMV multiplication phenotype of these selected F2 plants was determined by examining the accumulation levels of TMV-Cg CP in inoculated F3 plants by SDS-PAGE as described by Ishikawa et al. [M. Ishikawa, F. Obata, T. Kumagai, T. Ohno, Mol. Gen. Genet. 230, 33 (1991)].

The CAPS marker T18ISX (FIG. 1A) which gave an XbaI fragment length polymorphism between ecotypes Col-0 and WS, was created based on the finding that the end probe of the P1 clone 78E9 (FIG. 1C) showed an XbaI frangment length polymorphism between Col-0 and WS, and on the sequence information from the ESSA II BAC contig (FIG. 1B). Primers for T18SX were, T18SXF (5'-CTGAGAATGTTTATCCCAGCTG-3') (SEQ ID NO: 7) and T18SXR (5'-GTAATGCTTGAATCTCTTGATATC-3') (SEQ ID NO: 8). The PCR markers, g3883 and JGB9 are described in the *Arabidopsis thaliana* Database (AtDB). The *A. Thaliana* tom1-3 mutant was isolated by screening the Feldmann T-DBA-insertion library [K. A. Feldmann and M. D. Marks, Mol. Gen. Genet. 208, 1 (1987)] for mutants with low-level accumulation or TMV-Cg coat protein (CP). The tom1-3 plants showed similar accumulation patterns of TMV-Cg CP to thos in *A. thaliana tom*1-1 and tom1-2 plants. Genetic analysis suggested the causal mutation was within the TOM1 locus. the tom1-3 mutation was not linked with the T-DNA insertion. Fine mapping of the TOM1 locus was performed using the tom1-3 mutant as follows: DNA was prepared form one of the leaves of each F2 plant derived from a cross between tom1-3 (derived from ecotype WS) and the *A. thaliana* ecotype Col-0using the NaOH extraction method [H. Wang, M. Qi, A. J. Cutler, Nucleic Acids Res. 21, 4153 (1993)]. The genotype for markers g3883 and T18SX was subsequently examined for each F2 plant, and from 3103 original F2 plants, 246 plants which had a cromosomal recombination between these two markers were selected. DNA was then obtained from five leaves of each selected F2 plant, using the CTAB extraction method [S. O. Rogers and J. Bendich, Plant Mol. Biol. 5, 69 (1985)], and purified by chloroform extraction, isopropanol preciptation and $MgCl_2$ precipitation [T. Yamamoto and M. Horikoshi, Nucleic Acids Res. 23, 3351 (1995)]. Using this DNA, genotypes for the CAPS marker JGB9 and RFLP markers indicated in FIG. 1 were determined. The RFLP markers were prepared from the P1 genomic clones by restriction digestion. Information on the RFLP markers is available upon request. Preparation ofprobes and Southern hybridization were carried out using a Gene Images labeling and detection system (Amersham Pharmacia Biotech, Uppsala, Sweden). the TMV multiplicationphenotype of these selected F2 plantswas determined by examining the accumulation levels of TMV-Cg CP in inoculated F3 plants by SDS-PAGE as described by Ishikawa et al. [M. Ishikawa, F. Obata, T. Kumagai, T. Ohno, Mol. Gen. Genet. 230, 33 (1991)].

Through this analysis, the TOM1 locus was mapped to an approximately 22 kb region containing the JGB9 marker as shown in FIG. 1D. This region was covered by overlapping P1 genormic clones (FIG. 1C), which were subsequently subcloned into a T-DNA vector (FIG. 1E). An *Arabidopsis thaliana* genomic library constructed using a PI cloning system was obtained from Mitsui Plant Biotechnology Research Institute, and the screening for clones hybridizing with the JGB9 sequence and subsequent chromosome walking was carried out as described by Liu et al. [Y. G. Liu, N. Mitsukawa, A. Vazquez-Tello, R. F. Whittier, Plant Journal 7, 351 (1995)]. T-DNA clones 508 and 653 were constructed by partially digesting the P1 genomic clones 8C3 and 5F6, respectively, with EcoRI followed by subcloning into the T-DNA vector pCLD04541. T-DNA clones 1001 and X1112 were constructed by digesting the P1 genomic clones 8C3 with SalI+ClaI and 5F6 with XhoI, respectively, followed by subcloning into pCLD04541.

Recovery of TMV Multiplication Efficiency by Gene Transformation

The genomic DNA fragments cloned into the T-DNA vector were stably transformed into tom-1 plants using the vacuum infiltration method mediated by *Agrobacterium tumefaciens.*

T-DNA clones were electroporated into *Agrobacterium tumefaciens* C58C1 (pGV2260), and used to transform *A. thaliana* plants by the vacuum infiltration method [N. Bechtold and G. Pelletier, Methods Mol. Biol. 82, 259 (1993)].

Introduction of T-DNAs derived from the clones 1001 or X1112 resulted in the recovery of TMV multiplication efficiency to wild-type levels in the T1 generation, whereas that of clones 653 or 508 did not. All of the T2 plants in which TMV multiplication was recovered carried the NPTII gene that was present within the T-DNAs as far as the inventors examined (FIG. 1F).

TMV-Cg [T. Yamanaka et al., Virus Genes 16, 173 (1998)] was used for the TMV assay. The conditions for plant growth, inoculation with TMV-Cg, and determination of the levels of TMV-Cg CP accumulation by SDS-PAGE were as described by Ishikawa et al. [M. Ishikawa, F. Obata, T. Kumagai, T. Ohno, Mol. Gen. Genet. 230, 33 (1991)]. Five to eight T2 plants were used to determine the TMV multiplication phenotype for each transformed line. The presence of the NPTII gene sequence in T2 plants was examined in 2 and 4 of the complemented lines transformed by 1001 and X1112, respectively.

Figure 2:
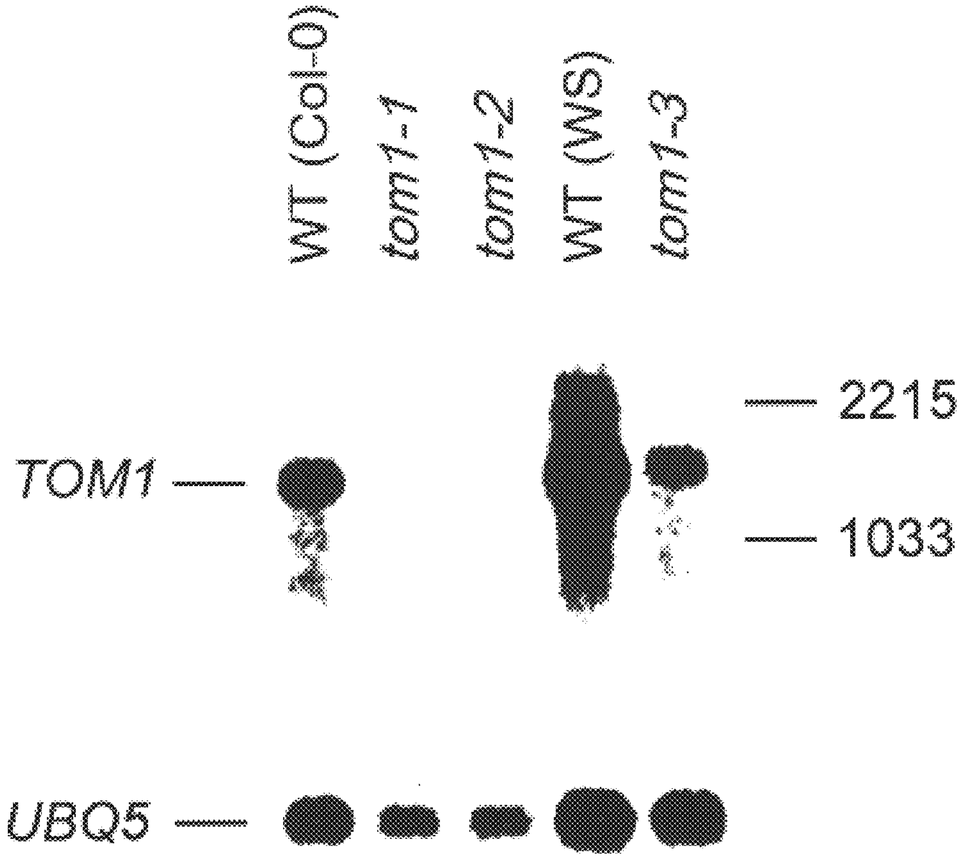
FIG. 2 is a picture of northern hybridization analysis, showing expression of TOM1 mRNA.

These data suggest that the TOM1 gene is located within the 6 kb region shared by the clones 1001 and X1112 (FIG. 1). Northern blot hybridization using this 6 kb region as a probe detected a single RNA species of approximately 1.4 kb in the total RNA from non-infected wild-type plants (data not shown; similar to FIG. 2).

Total RNA was extracted from frozen plant tissues and purified using ISOGEN LS (Nippon Gene, Tokyo, Japan) according to the manufacturer's instructions. Northern blotting and hybridization was performed ,is described by Ishikawa et al. [Ishikawa, S. Naito, T. Ohno, J. Virol. 67, 5328

(1993)]. $^{32}$P-labelled probes were prepared using a Multiprime DNA labelling system (Amersham Pharmacia Biotech, Uppsala, Sweden).

Northern Blot Hybridization Analysis Showing Expression of the TOM1 mRNA.)

Total RNA was extracted from aerial tissues of 3- to 4-week-old wild-type and mutant plants as indicated above the panels, denatured by glyoxal, separated by 1% agarose gel electrophoresis and blotted onto a nylon membrane. Duplicate blots were prepared and were probed with $^{32}$P-labelled DNAs hybridizing with either TOM1 or UBQ5 [E. E. Rogers and F. M. Ausubel, Plant Cell 9, 305 (1997)] sequences. To prepare the TOM1-specific probe, a DNA fragment corresponding to the predicted TOM1 ORF was amplified by PCR from a cDNA clone and gel-purified. The positions of TOM1 and UBQ5 mRNAs are indicated on the left. The positions of CMV RNA3 (2215 nucleotides) and RNA4 (1033 nucleotides) used as size markers are shown on the right.

In tom1-1, -2 and -3 plants, the accumulation levels of the 1.4 kb RNA were lower than those in the wild-type plants (FIG. 2), suggesting that the band in the wild-type lane represents an RNA species derived from the TOM1 locus. The presence of the RNA in non-infected plants is consistent with our previous results suggesting that TOM1 function is necessary at very early stages after viral inoculation to establish infection [M. Ishikawa, S. Naito, T. Ohno, J. Virol. 67, 5328 (1993)].

Determination of TOM1 Base Sequence

Sequencing of cDNA clones hybridizing with the complementing 6 kb region and comparison of the sequence with expressed sequence tag (EST) and genomic sequence data revealed a 1226-nucleotide mRNA sequence consisting of 11 exons.

The inventors screened an *Arabidopsis thaliana* 5'-STRETCH cDNA library (Clontech, Palo Alto, Calif., USA) containing $1\times10^5$ plaques for clones hybridizing with the overlapping region of the inserts of T-DNA clones 1001 and X1112, and obtained two such cDNA clones. Inserts of the cDNA clones were amplified by PCR and sequenced. Primers used to amplify and sequence the cDNA inserts were: 5'-CGCCTCCATCAACAAACTTTCTTG-3'(SEQ ID NO:9) and 5'-GTTCTGGTAAAAAGCGTGGTC-3'(SEQ ID NO:10). A 377 DNA sequencer and BigDye terminator sequencing kit (Perkin Elmer, Applied Biosystems division, Foster City, Calif., USA) were used for sequencing. There was an overlap between these cDNA inserts, which covered a 1064-nucleotide region in total (GenBank # AB016925). An Arabidopsis WU-BLAST2 search against the sequence detected three expressed sequence tag clones [T. Newman et al., Plant Physiol. 174, 1241 (1994)]: 120J4T7 (GenBank accession number T43509), 160I24T7 (GenBank # T88633) and 119P7T7 (GenBank # T43917). By assembling these sequences, a total region of 1226 nucleotides was identified. Comparison with the genomic sequence (Genbank # AB016924) suggested that the 1226-nucleotide sequence was composed of 11 exons.

Considering the size of the corresponding mRNA estimated by Northern blot hybridization analysis and the length of polyA tail, the sequence was likely to cover most of the mRNA. Within the mRNA sequence, an open reading frame (ORF) of 876 nucleotides (291 amino acids) which started at the first AUG codon from the terminus was found. The determined nucleotide sequence of TOM1 is shown in SEQ ID NO:2 in a sequence list.

There was an in-frame translation termination codon upstream of the ORF, denying the possibility of translation initiation from an upstream AUG codon which could be present in a region that was not cloned in the cDNAs.

Furthermore, all three tom1 alleles had mutations within the genomic region corresponding to the ORF, and each mutation was suggested to affect the ORF severely. The tom1-1, tom1-2 and tom1-3 consist of a point mutation at the splicing acceptor site in the intron 5, a nonsense mutation in exon 2, and one base frame-shifting insertion in exon 4, respectively (GenBank accession numbers AB016924 and AB016925). These results show that the ORF encodes the TOM1 product.

Structural Characterization of the TOM1 Protein

The deduced amino acid sequence of the TOM1 protein is shown in a SEQ ID NO: 1 in a sequence list and in FIG. 3. Boxes and underlines represent putative membrane-spanning regions and cytoplasmic regions, respectively, predicted by the Predict-Protein program [B. Rost, R. Casadio, P. Fariselli, C. Sander, Protein Science 4, 521 (1995)]. Similar results were obtained using SOSUI program [T. Hirokawa, S. Boon-Chieng, S. Mitaku, Bioinformatics 14, 378 (1998)]. Asparagine residues marked by asterisks are putative glycosylation sites.

The deduced amino acid sequence of the TOM1 protein contained several highly hydrophobic regions. Analysis with a computer program that predicts transmembrane regions and their topology (PHDhtm/PredictProtein: B. Rost, R. Casadio, P. Fariselli, C. Sander, Protein Science 4, 521 (1995); SOSUI: T. Hirokawa, S. Boon-Chieng, S. Mitaku, Bioinformatics 14, 378 (1998) suggested that the protein is a seven-pass transmembrane protein with its C-terminus exposed in the cytoplasm.

In FIG. 3, Boxes and underlines represent putative membrane-spanning regions and cytoplasmic regions, respectively, predicted by the Predict-Protein program [B. Rost, R. Casadio, P. Fariselli, C. Sander, Protein Science 4, 521(1995)]. Two typical consensus sequences for N-glycosylation were present at amino acids 28–31 and 168–171, both of which were located in the region, predicted to be exoplasmic (FIG. 3). No apparent N-terminal or other signal sequences necessary for targeting to organelles were found in the sequence (PSORT: K. Nakai and M. Kanehisa, Genomics, 14, 897 (1992).

Database searches for proteins with similar amino acid sequences to that of TOM1 listed integral membrane proteins only with weak similarity.

Database searches for amino acid sequences which showed a similarity to the deduced amino acid sequence of the TOM1 protein was performed using the following three programs: BLAST 2.0 [S. F. Alschul et al., Nucleic Acids Res. 25, 3389 (1997), ] detected a weak similarity to a putative seven pass transmembrane protein TM7SF1 from human [C. Spangenberg, A. Winterpacht, B. U. Zabel, R. W. Loebert, Genomics 48, 178 (1998)]; Fasta 3 [W. R. Pearson and D. J. Lipman, Proc. Natl. Acad. Sci. U.S.A. 85, 2444 (1988)] detected a weak similarity to cytochrome b from many eukaryotic organisms; PropSearch [U. Hobohm and C. Sander, J. Mol. Biol. 251, 390 (1995)] listed the PnuC protein of Salmonella typhimurium, a nicotinamiele mononucleotide transporter with putative seven membrane-spanning regions [J. W. Foster, Y. K. Park, T. Fenger, M. P. Spector, J. Bacteriology 172, 4187 (1990).] with the highest score (distance=8.41), along with other membrane proteins, most of which were receptors or transporters. It is speculated that these hits represent structural similarity among integral membrane proteins.

The Function of the TOM1 Protein

Previous analyses utilizing protoplasts suggested that the tom1 mutation affects the multiplication of TMV RNA within a single cell in a process after the initial uncoating of the genomic RNA such as RNA replication [M. Ishikawa, S. Naito, T. Ohno, J. Virol. 67, 5328 (1993)]. The replication of most or all positive-strand RNA viruses including TMV is thought to occur in membrane-bound complexes [K. W. Buck, Advances in Virus Research 47, 159 (1996)., T. A. Osman and K. W. Buck, J. Virol. 70, 6227 (1996).].

However, the replication proteins of TMV do not have apparent membrane-spanning domains nor consensus amino acid sequences for modifications to function as an anchor on membranes [(B. Rost, R. Casadio, P. Fariselli, C. Sander, Protein Science 4, 521(1995); T. Hirokawa, S. Boon-Chieng, S. Mitaku, Bioinformatics 14, 378 (1998); K. Nakai and M. Kanehisa, Genomics, 14, 897 (1992)]). Therefore, the TMV-encoded replication proteins are likely to function in association with host proteins localized on membranes. While the results do not show whether the TOM1 protein directly participates in TMV RNA replication or influences replication by some more indirect effect, one possibility is that TOM1 may link the viral replication machinery to membranes.

At present, several host proteins have been suggested to contribute to the replication of alpha-like viruses, including, for BMV, the p41 subunit of eukaryotic initiation factor 3 (eIF3) of barley [R. Quadt et al., Proc. Natl. Acad. Sci. USA 90, 1498 (1993)] and yeast MAB 1 and MAB2 proteins [M. Ishikawa, J. Diez, M. A. Restrepo-Hartwig, P. Ahlquist, Proc. Natl. Acad. Sci. U.S.A. 94, 13810 (1997)23, J. Diez, M. Ishikawa, M. Kaido, P. Ahlquist, unpublished results]; for TMV, the GCD10-related subunit of eIF3 of tomato [T. A. Osman and K. W. Buck, J. Virol. 71, 6075 (1997)]; for Sindbis virus, mosquito homolog of the La autoantigen [N. Pardigon and J. H. Strauss, J. Virol. 70, 1173 (1996)].

Among them, the TOM1 protien is the only apparent integral membrane protein [B. Rost, R. Casadio, P. Fariselli, C. Sander, Protein Science 4, 521(1995); T. Hirokawa, S. Boon-Cheng, S. Mitaku, Bioinformatics 14, 378 (1998)]. Synthesis of BMV RNA takes place on endoplasmic reticulum (ER) membranes [M. A. Restrepo-Hartwig and P. Ahlquist, J. Virol, 70, 8908 (1996)], whereas that of TYMV or alfalfa mosaic virus RNA occurs on the cytoplasmic surface of chloroplast outer membrane [M. deGraaff, L. Coscoy, E. M. J. Jaspars, Virology 194, 878 (1993); M. Garnier, R. Ramoun and J. M. Bove, Virology 104, 374 (1980)]. The replication proteins of TMV and alphavirus localize on ER and endosome/lysosome membranes, respectively [M. Heinlein et al., Plant Cell 10, 1107 (1998); S. Froshaur, J. Kartenbeck, A. Helenius, J. Cell Biol. 107, 2075 (1988)], although the sites of RNA synthesis have not been determined.

Therefore, even among closely-related alpha-like viruses, the intracellular sites of viral RNA synthesis may be divergent. If so, membrane anchors of viral replication complexes may also be divergent. It is plausible that the replication complexes of CMV and TYMV, alpha-like viruses related to TMV, are linked to membranes by host factors distinct from TOM1, explaining why the tom1 mutation does not affect the multiplication of these viruses [M. Ishikawa, F. Obata, T. Kumagai, T. Ohno, Mol. Gen. Genet. 230, 33 (1991)].

Figure 4:
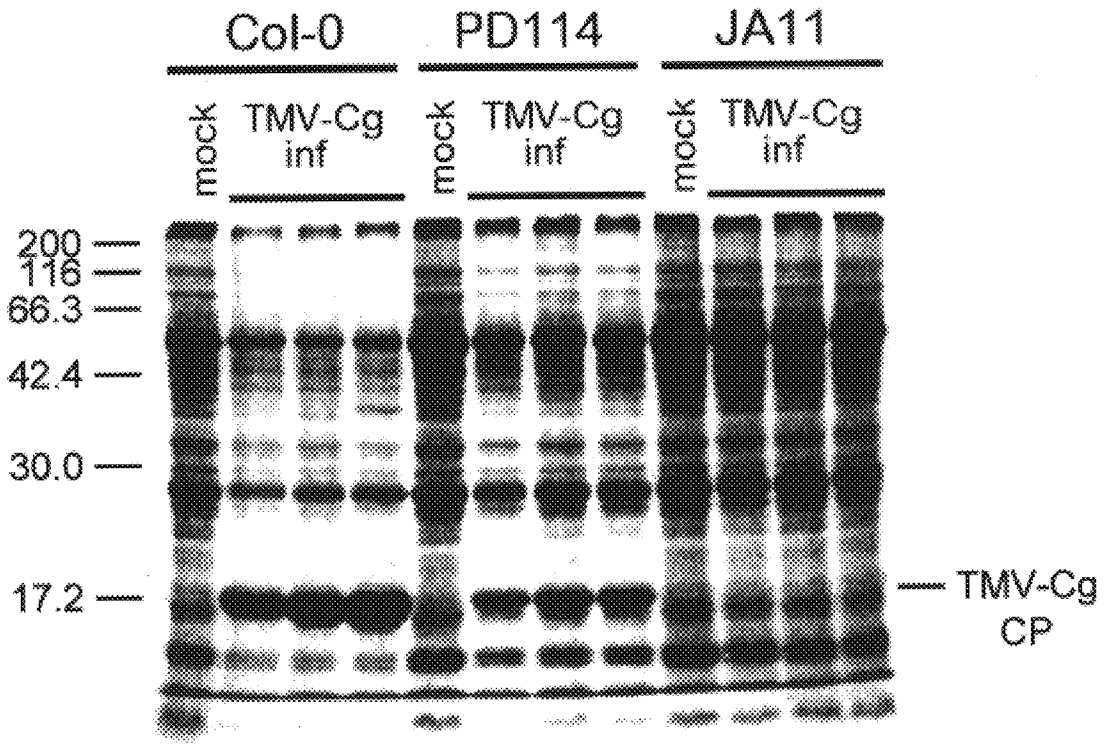
FIG. 4 is a picture showing accumulation of TMV-Cg in each mutant strain.

In spite of almost complete damage of TOM1 gene function in either of tom-1, tom-2 or tom-3 mutant strain of arabidopsis thaliana, the ability to multiplicate TMV-Cg strain still remains. The accumulation of TMV-Cg CP in the mutant strains is about fourth part compared to that in the wild-type strain in a plant body at the 16th day of cultivation (referred to FIG. 4). This result indicates that TOM1 gene product is indispensable for multiplication of TMV or remaining ability to multiplicate TMV is borne by a certain gene similar to TOM 1. Then the tom1-1 mutant strain was further treated by ethylmethane sulfonate to obtain JA11 strain wherein the ability to multiplicate TMV is almost completely abolished (FIG. 4). The TMV-Cg was inoculated to Col-0 wild type strain and each mutant strain, total protein of a non-inoculated upper leaf was separated by SDS-PAGE analysis at the 16th day of inoculation, accumulation of TMV-Cg CP was measured by Coomassie brilliant blue staining. The result is shown in FIG. 4. In FIG. 4, mock indicates non-inoculated control plant, whereas PD114 indicates the tom1-1 mutant strain. The ethylmethane sulfonate treatment was performed by treatment of seeds in 0.3% ethylmethane sulfonate at 20° C. for 16 hours [Kranz, A. R. and Kirchheim, B. (1987) Genetic resources in Arabidopsis. Arabidopsis Inf. Serv. vol 24, section 4.2, pp 1–7.]. Genetic analysis revealed existence of recessive mutation of tom3-1, which results in further decline of TMV multiplication compared to single tom1 mutation.

Identification of TOM3 Gene

Figure 5:
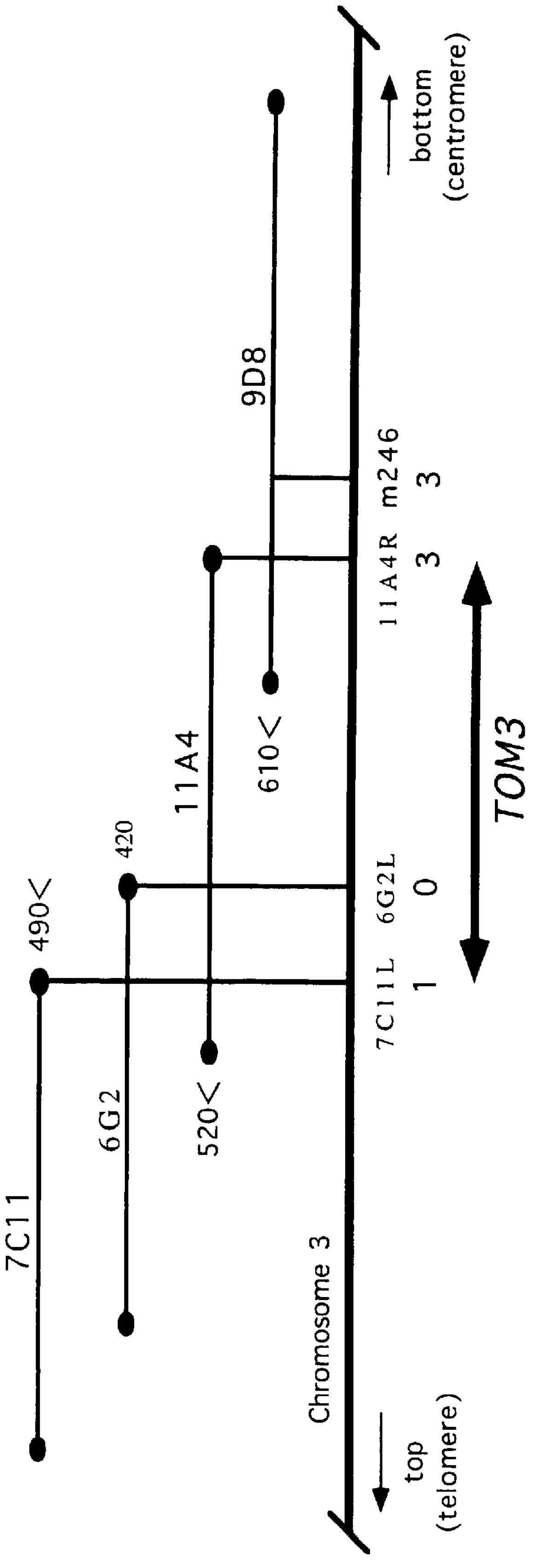
FIG. 5 is a schematic figure showing mapping of TOM3 gene.

By genetic mapping, tom3-1 mutation was localized between RFLP markers 7C11L and 11A4R (FIG. 5) on yeast artificial chromosome (YAC) clone CIC11A4 (insert size : about 520 kbp), of which insert covers a top region of chromosome 2. Twelve lines exhibited tom-1 tom-3 phenotype in F2 lines produced by a cross of the JA11 strain and the tom1-3 mutant strain. The mapping was achieved by genotype investigation of each marker in the 12 lines described above. In FIG. 5, the RF, LP markers and numbers of recombination occurred between the markers and the tom3 mutation are illustrated under line of chromosome 3. The horizontal lines, wherein the both ends are pointed by closed circles, indicate the yeast artificial chromosome (YAC) clones. The numbers illustrated next to lines of YAC indicate approximate sizes (kbp) of the YAC inserts. As described above, the TOM3 gene was mapped between 7C11L and 11A4R.

Through BLAST search, the EST clone 86D11 was found to encode an amino acid sequence with high homology to TOM1. In addition, the genomic sequence corresponding to 86D11 was positioned on an *A. thaliana* genomic bacterial artificial chromosome (BAC) clone F504 existing near CIC11A4.

From these observations, the TOM1 homologous sequence may be related to TOM3. Since the cDNA insert of 86D11 was very short, it was not likely that the whole sequence of mRNA was covered by 86D11. Therefore plaque hybridization [Ausubel et al. (1994). Current protocols in molecular biology. John Wiley & Sons, Inc., New York, N.Y., USA.)] was performed to screen *Arabidopsis thaliana* 5'-STRETCH cDNA library (Clonetech, Palo Alto, Calif., USA) using 86D11 as a probe. As the result of hybridization, five positive clones were obtained. The nucleotide sequences of the inserted DNA of the cDNA a clones were determined, and by assembling them, a 1203 bp sequence was identified which was assumed to correspond to almost full-length mRNA. From the nucleotide sequence of the cDNA obtained, the corresponding niRNA was revealed to encode a protein which consists of 303 amino acids having similarity to TOM1 protein. The deduced amino acid sequence of TOM1 protein and that of TOM3 protein are shown in FIG. 6, in comparison with each other. In FIG. 6, the identical amino acid residues between TOM1 and TOM3 are indicated by double dots, whereas the similar amino acid residues are indicated by single dots.

Further, the genomic nucleotide sequence of the TOM1 homologous region was compared between the wild type strain and the JA11 mutant strain. In the JA11 mutant strain, the 45th tryptophan codon (TGG) was mutated to nonsense codon (TAG), which is assumed to cause lethal effect on expression of the protein. From the results, the gene corresponding to open reading frame (ORF) shown in FIG. 6 is suggested to be TOM3. The nucleotide sequence of TOM3 gene is shown in sequence number 4 in a sequence list, and the deduced amino acid sequence of TOM3 protein is shown in sequence number 3 in a sequence list.

Relationship Between the TOM1 Gene and the TOM3 Gene

The amino acid sequence encoded by the TOM3 gene has more than 50% identity to TOM1. Then, the TOM3 protein is assumed to have parallel function in multiplication of TMV. Moreover, the multiplication of TMV is almost completely abolished in the tom1 tom3 double mutant strain, the function of TOM1/TOM3 proteins is assumed to be indispensable for multiplication of TMV. In addition, the double mutant strain was able to grow only slightly slower than the wild-type plants. Considering heavy distortion of the expression of both genes, the result is surprising. Therefore, it is suggested that almost complete resistance against a virus might be rendered to a plant of various species by inactivation of genes similar to TOM1 gene, without harmful effect on its growth ability.

This invention provides the TOM1 gene identified by a nucleotide sequence referred to sequence number 2 in a sequence list, and also provides the TOM1 protein, encoded by the gene, identified by an amino acid sequence referred to sequence number 1 in a sequence list. Further, this invention provides the TOM3 gene identified by a nucleotide sequence referred to sequence number 4 in a sequence list, and also provides the TOM3 protein, encoded by the gene, identified by an amino acid sequence referred to sequence number 3 in a sequence list. The TOM1 gene and the TOM3 gene are derived from *Arabidopsis thaliana* and coding proteins indispensable for multiplication of tabacco mosaic virus. Therefore, a plant having resistance against a virus can be produced by alteration of the genes.

What is claimed is:

1. An isolated DNA molecule consisting of:

a nucleotide sequence consisting of nucleotide numbers from 1 to 876 in SEQ ID NO.:2 or, a nucleotide sequence that hybridizes with said nucleotide sequence of SEQ ID NO.:2 and encodes a protein having activity to induce the multiplication of an alpha-like virus in a host plant cell.

2. A transgenic plant comprising a gene defined by DNA molecule according to claim 1 wherein the expression of said gene is inhibited in said plant to render resistance against an alpha-like virus.

3. An isolated DNA molecule consisting of:

a nucleotide sequence consisting of nucleotide numbers from 1 to 912 in SEQ ID NO.:4 or, a nucleotide sequence that hybridizes with said nucleotide sequence of SEQ ID NO.:4 and encodes a protein having activity to induce the multiplication of an alpha-like virus in a host plant cell.

4. A transgenic plant comprising a gene defined by DNA molecule according to claim 3 wherein the expression of said gene is inhibited in said plant to render resistance against an alpha-like virus.

* * * * *

SEQUENCE LISTING

```
<160> NUMBER OF SEQ ID NOS:  10

<210> SEQ ID NO 1
<211> LENGTH: 291
<212> TYPE: PRT
<213> ORGANISM: Arabidopsis thaliana heynh

<400> SEQUENCE: 1

Met Thr Asp Ser Gly Leu Met Met Pro Ala G lu Ile Ala Gly Ile Leu
  1               5                  10                  15

Thr Thr Ala Ile Thr Ser Trp Trp Asp Asp V al Asn Glu Ser Thr Gln
             20                  25                  30

Trp Gln Asp Gly Ile Phe Phe Ala Leu Cys G ly Ala Tyr Ala Leu Val
         35                  40                  45

Ser Ala Val Ala Leu Val Gln Leu Ile Arg I le Gln Met Arg Val Pro
     50                  55                  60

Glu Tyr Gly Trp Thr Thr Gln Lys Val Phe H is Leu Met Asn Phe Val
 65                  70                  75                  80

Val Asn Gly Val Arg Ala Val Leu Phe Gly P he His Met Gln Val Phe
                 85                  90                  95

Leu Val His Pro Lys Ala Leu Cys Trp Val L eu Leu Asp Leu Pro Gly
            100                 105                 110

Leu Leu Phe Phe Ser Ala Tyr Thr Leu Leu V al Leu Phe Trp Ala Glu
        115                 120                 125

Ile Tyr His Gln Ala Arg Ser Leu Pro Thr A sp Lys Leu Arg Ile Thr
    130                 135                 140

Tyr Ile Ser Val Asn Val Ala Val Tyr Leu A la Gln Ile Gly Ile Trp
145                 150                 155                 160

Ala Tyr Ile Trp Val His Asp Asn Ser Thr V al Glu Leu Val Gly Lys
                165                 170                 175

Ile Phe Ile Ala Val Val Ser Phe Ile Ala A la Leu Gly Phe Leu Leu
            180                 185                 190
```

-continued

```
Tyr Gly Gly Arg Leu Phe Phe Met Leu Arg A rg Phe Pro Ile Glu Ser
        195                 200                 205

Lys Gly Arg Arg Lys Lys Leu His Glu Val G ly Ser Val Thr Ala Ile
    210                 215                 220

Cys Phe Thr Cys Phe Leu Ile Arg Cys Val V al Val Ala Val Ser Ala
225                 230                 235                 240

Phe Asp Lys Asp Leu Thr Leu Asp Val Leu A sp His Pro Val Leu Asn
                245                 250                 255

Leu Ile Tyr Tyr Met Val Val Glu Val Leu P ro Ser Ala Leu Val Leu
            260                 265                 270

Phe Ile Leu Arg Lys Leu Pro Pro Lys Arg V al Ser Ala Gln Tyr His
        275                 280                 285

Pro Ile Gln
    290


<210> SEQ ID NO 2
<211> LENGTH: 876
<212> TYPE: DNA
<213> ORGANISM: Arabidopsis thaliana heynh

<400> SEQUENCE: 2

atgacggatt cgggtctaat gatgccggcg gagattgctg gaattctaac c acggcgatt     60

acgagttggt gggatgatgt taatgagtca actcagtggc aagatgggat c tttttcgct    120

ctttgtggtg cttatgctct tgtttccgcc gttgctcttg ttcaactgat a aggatccaa    180

atgagagtgc ctgagtatgg ttggactact cagaaggtgt ttcatcttat g aactttgtc    240

gtcaatggag ttcgtgcggt tctgtttgga tttcacatgc aagtatttct t gttcatccc    300

aaggctcttt gctgggtact attggatctt cctggccttc tctttttctc g gcatacacg    360

ctgcttgtgc tgttctgggc agagatatat caccaggcta gaagcttacc t acagataag    420

ctgcggataa cctatatttc tgtcaacgtg gctgtatatt tggctcagat t ggtatctgg    480

gcatacatct gggtacatga taacagcact gtggagttag ttggaaagat a tttatcgca    540

gttgtgtctt tcatcgccgc attaggcttc ttgctgtatg gaggaagatt g tttttcatg    600

ctaagaaggt tccctatcga gtcaaaagga agaaggaaga aactccacga g gttggatct    660

gtgacagcta tatgcttcac ctgcttcctc ataagatgcg ttgtggtggc t gtatcagct    720

tttgacaagg atttaacact tgatgttctt gatcatccgg ttctgaactt a atctactat    780

atggtggtag aagtacttcc atcggcacta gtcctcttca ttctccgaaa g ctacctcca    840

aagagagtat cagctcaata ccatccgatc cagtag                              876


<210> SEQ ID NO 3
<211> LENGTH: 303
<212> TYPE: PRT
<213> ORGANISM: Arabidopsis thaliana heynh

<400> SEQUENCE: 3

Met Arg Ile Gly Gly Val Glu Val Thr Lys P he Ala Ser Glu Met Met
  1               5                  10                  15

Ser Ser Ser Ser Ser Ser Ala Val Glu Met L eu Asn Leu Lys Glu Ala
            20                  25                  30

Ser Asn Trp Trp Ser Asp Val Asn Glu Ser P ro Ile Trp Gln Asp Arg
        35                  40                  45

Ile Phe His Val Leu Ala Val Leu Tyr Gly I le Val Ser Leu Val Ala
    50                  55                  60
```

-continued

Val Ile Gln Leu Val Arg Ile Gln Leu Arg V al Pro Glu Tyr Gly Trp
65 70 75 80

Thr Thr Gln Lys Val Phe His Phe Leu Asn P he Val Val Asn Gly Val
85 90 95

Arg Ala Val Val Phe Val Phe Arg Arg Asn V al Gln Phe Met Gln Pro
100 105 110

Glu Ile Leu Gln His Ile Leu Leu Asp Ile P ro Ser Leu Ala Phe Phe
115 120 125

Thr Thr Tyr Ala Leu Leu Val Leu Phe Trp A la Glu Ile Tyr Tyr Gln
130 135 140

Ala Arg Ala Val Ser Thr Asp Gly Leu Arg P ro Ser Phe Phe Thr Ile
145 150 155 160

Asn Ala Val Val Tyr Val Val Gln Ile Ala L eu Trp Leu Val Leu Trp
165 170 175

Trp Lys Pro Val Arg Val Met Val Ile Leu S er Lys Met Phe Phe Ala
180 185 190

Gly Val Ser Leu Phe Ala Ala Leu Gly Phe L eu Leu Tyr Gly Gly Arg
195 200 205

Leu Phe Leu Met Leu Gln Arg Phe Pro Val G lu Ser Lys Gly Arg Arg
210 215 220

Lys Lys Leu Gln Glu Val Gly Tyr Val Thr T hr Ile Cys Phe Thr Cys
225 230 235 240

Phe Leu Ile Arg Cys Ile Met Met Cys Phe A la Ala Phe Asp Glu Gly
245 250 255

Ala Asn Leu Asp Val Leu Asp His Pro Ile L eu Asn Phe Ile Tyr Tyr
260 265 270

Leu Leu Val Glu Ile Leu Pro Ser Ser Leu V al Leu Phe Ile Leu Arg
275 280 285

Lys Leu Pro Pro Lys Arg Gly Ile Thr Gln T yr His Gln Ile Arg
290 295 300

<210> SEQ ID NO 4
<211> LENGTH: 912
<212> TYPE: DNA
<213> ORGANISM: Arabidopsis thaliana heynh

<400> SEQUENCE: 4
atgagaatcg gcggcgtcga ggttacgaaa tttgcgtcgg agatgatgtc g tcgtcgtct 60 tcgtcggcgg tggagatgtt gaatctcaaa gaagcttcga attggtggtc a gacgtaaac 120 gaatctccga tttggcagga tcgtatcttc catgttctcg ctgttctcta c ggaatcgtt 180 tccctcgttg ctgtgattca acttgtgaga atacaattga gagttcctga a tatggttgg 240 acgacgcaaa aggtctttca ctttctcaat ttcgttgtta atggagttcg t gctgtggtg 300 tttgtcttca ggcgaaatgt tcagtttatg caaccagaga ttctgcaaca t atcttgctt 360 gatattccaa gtcttgcttt cttcaccacc tatgctcttc tggttctttt c tgggctgaa 420 atttattatc aggcgcgtgc agtatcgact gatggactca ggccaagctt c ttcacaatt 480 aatgcagttg tatatgtagt tcagattgct ctatggttgg ttttgtggtg g aagcctgtt 540 cgagttatgg taatcctatc taagatgttc tttgcaggtg tttcattgtt c gctgccctt 600 ggatttttac tttatggtgg aaggcttttc ctaatgttgc aacggtttcc a gtagaatct 660 aaagggcggc gcaaaaagct gcaagaggtt ggttacgtga caaccatatg c tttacgtgt 720 ttcctcatca gatgtatcat gatgtgcttt gctgctttcg atgagggggc a aaccttgat 780

-continued gtgttagatc accccatcct taacttcata tattacctgt tggtagagat a ttaccctcc 840 tctctggtcc tcttcatctt gagaaagcta ccaccaaaac gaggcattac a caataccat 900 cagattcgct ga 912

<210> SEQ ID NO 5
<211> LENGTH: 25
<212> TYPE: DNA
<213> ORGANISM: Arabidopsis thaliana heynh

<400> SEQUENCE: 5
ctatgactgg gcacaacaga caatc 25

<210> SEQ ID NO 6
<211> LENGTH: 20
<212> TYPE: DNA
<213> ORGANISM: Arabidopsis thaliana heynh

<400> SEQUENCE: 6
gcgatagaag gcgatgcgct 20

<210> SEQ ID NO 7
<211> LENGTH: 22
<212> TYPE: DNA
<213> ORGANISM: Arabidopsis thaliana heynh

<400> SEQUENCE: 7
ctgagaatgt ttatcccagc tg 22

<210> SEQ ID NO 8
<211> LENGTH: 24
<212> TYPE: DNA
<213> ORGANISM: Arabidopsis thaliana heynh

<400> SEQUENCE: 8
gtaatgcttg aatctcttga tatc 24

<210> SEQ ID NO 9
<211> LENGTH: 24
<212> TYPE: DNA
<213> ORGANISM: Arabidopsis thaliana heynh

<400> SEQUENCE: 9
cgcctccatc aacaaacttt cttg 24

<210> SEQ ID NO 10
<211> LENGTH: 21
<212> TYPE: DNA
<213> ORGANISM: Arabidopsis thaliana heynh

<400> SEQUENCE: 10
gttctggtaa aaagcgtggt c 21